United States Patent
Sanders

(10) Patent No.: US 9,964,550 B2
(45) Date of Patent: May 8, 2018

(54) AT-HOME BLOOD PREGNANCY TEST KIT

(71) Applicant: Melinda Sanders, Rochester, IN (US)

(72) Inventor: Melinda Sanders, Rochester, IN (US)

( * ) Notice: Subject to any disclaimer, the term of this patent is extended or adjusted under 35 U.S.C. 154(b) by 0 days. days.

(21) Appl. No.: 14/615,628

(22) Filed: Feb. 6, 2015

(65) Prior Publication Data

US 2015/0153366 A1 Jun. 4, 2015

Related U.S. Application Data

(60) Provisional application No. 61/941,083, filed on Feb. 18, 2014.

(51) Int. Cl.
*G01N 33/76* (2006.01)
*G01N 33/53* (2006.01)

(52) U.S. Cl.
CPC ......... *G01N 33/76* (2013.01); *G01N 33/5302* (2013.01); *G01N 2333/59* (2013.01)

(58) Field of Classification Search
CPC ......... G01N 2800/368; G01N 2400/02; G01N 33/689; G01N 33/74; G01N 33/743; A61D 17/006
See application file for complete search history.

(56) References Cited

U.S. PATENT DOCUMENTS

| 4,003,988 A | 1/1977 | Hoff | |
|---|---|---|---|
| 4,543,339 A | 9/1985 | O'Neill | |
| 5,998,220 A * | 12/1999 | Chandler | B01L 3/5023 422/408 |
| 7,300,802 B2 * | 11/2007 | Paek | C12Q 1/001 204/403.01 |
| 7,393,696 B2 * | 7/2008 | Roth et al. | 436/510 |
| 7,666,683 B1 | 2/2010 | Cole | |
| 2002/0013002 A1 | 1/2002 | D'Aurora | |
| 2004/0019301 A1 * | 1/2004 | Wong | A61B 5/145 600/584 |
| 2005/0148096 A1 | 7/2005 | Cole | |
| 2006/0029924 A1 * | 2/2006 | Brewster | G01N 33/54386 435/4 |
| 2006/0134804 A1 * | 6/2006 | Gao et al. | 436/514 |
| 2008/0124244 A1 * | 5/2008 | Sigel | G01N 33/558 422/400 |
| 2009/0253119 A1 * | 10/2009 | Zhou et al. | 435/5 |
| 2010/0015646 A1 * | 1/2010 | Johnson | G01N 33/558 435/7.92 |
| 2010/0323912 A1 * | 12/2010 | Korlach | C12Q 1/6825 506/9 |
| 2011/0039256 A1 * | 2/2011 | McGiven | G01N 33/542 435/5 |
| 2013/0217136 A1 * | 8/2013 | Nazareth et al. | 436/86 |

FOREIGN PATENT DOCUMENTS

WO WO2012/170435 A2 * 12/2012 ............. G01N 33/68

\* cited by examiner

*Primary Examiner* — Bao Thuy L Nguyen
*Assistant Examiner* — Ellen J Marcsisin
(74) *Attorney, Agent, or Firm* — Global Intellectual Property Agency, LLC; Jordan Sworen

(57) ABSTRACT

Disclosed is an at-home blood pregnancy test kit that can identify the presence of hCG in a blood sample to detect pregnancy in female mammals. The present kit includes a housing having a sample strip that is in fluid communication with a sample pad for holding a blood sample, a test pad, and a conjugate pad. The housing further includes a test window and a push button for releasing a reagent that can react with hCG. The reagent and the test pad include antibodies that can bind with hCG antigens to detect presence of the same. The test window is adapted to display a symbol that indicates a negative pregnancy test result in the absence of hCG, or display a symbol that indicates a positive pregnancy test result in the presence of hCG.

4 Claims, 1 Drawing Sheet

AT-HOME BLOOD PREGNANCY TEST KIT

CROSS REFERENCE TO RELATED APPLICATION

Figure 1:
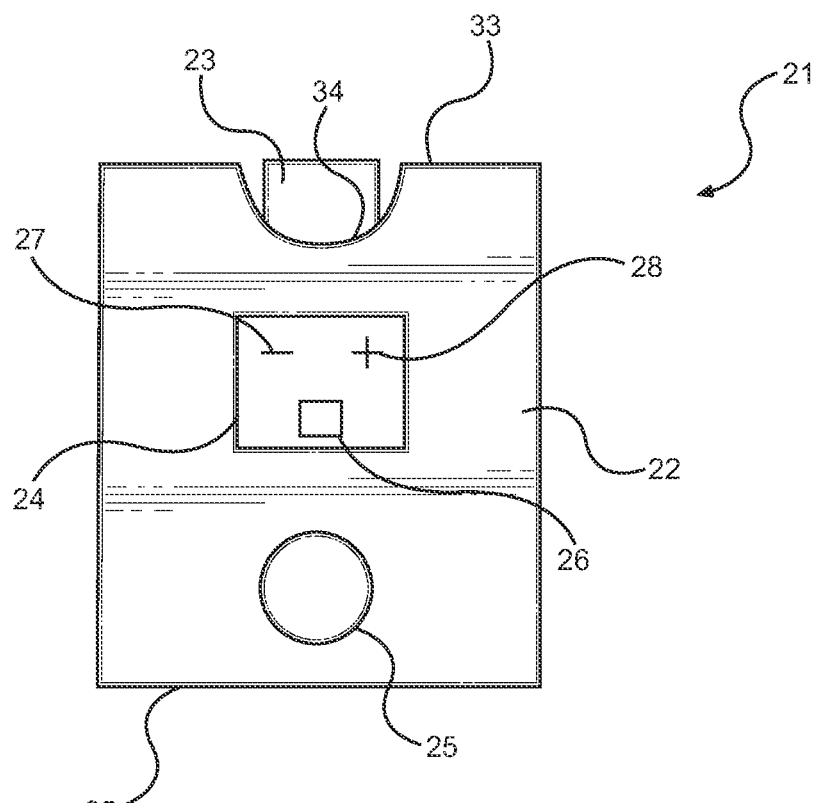

This application claims the benefit of U.S. Provisional Application No. 61/941,083 filed on Feb. 18, 2014. The above identified patent application is herein incorporated by reference in its entirety to provide continuity of disclosure.

BACKGROUND OF THE INVENTION

Field of the Invention

The present invention relates to a pregnancy test kit. More specifically, the present invention pertains to a portable pregnancy test kit that is suitable for home use. The present test kit is adapted to perform an hCG immunoassay to measure the presence of hCG in a blood sample, thereby detecting pregnancy. If a sufficient level of hCG is detected in the blood sample, the test kit can visually indicate the test result.

Pregnancy tests are designed to determine whether a woman is pregnant. Most pregnancy tests are designed to indicate whether a person's urine or blood contains a hormone called human chorionic gonadotropin (hCG). This hormone is produced after a fertilized egg attaches to the wall of a woman's uterus. In non-pregnant women, hCG levels are normally undetectable. If a woman is pregnant, however, levels of hCG continue to rise rapidly, doubling every two to three days.

Two main types of pregnancy tests are used to determine if a woman is pregnant: urine tests and blood tests. Urine tests can be done at home or in a doctor's office. Urine tests are known to detect hCG traces as low as 10 mIU/mL to 100 mIU/mL, and they are approximately 97 percent accurate when performed correctly. Urine tests are widely used because they can be done in the privacy and convenience of a home, they give a fast result, and are easy to use. However, urine tests detect a pregnancy later than blood tests because urine tests are generally taken about a week after a missed menstruation, and if done incorrectly, the result can be inaccurate.

Blood tests are much more accurate than urine tests, and blood tests can detect a pregnancy earlier than urine tests, or only about six to eight days after ovulation. Additionally, blood tests can measure the concentration of hCG hormone in a woman's blood, which can be useful for tracking certain problems in pregnancy. However, blood tests take longer to produce a result, and are generally performed in a doctor's office. Thus, a blood test kit for use at home to increase the privacy and convenience of a user is desired.

The present invention provides a blood pregnancy test kit that is suitable for home use. The present test kit comprises a qualitative hCG test kit, which can detect presence of hCG in a blood sample of a female mammal. The blood pregnancy test kit comprises a housing having an upper end with an opening, a lower end, a top side, a bottom side, and a defined interior volume having a sample pad, a test pad, and a conjugate pad. The opening comprises a sample strip, which extends outward therefrom. The sample strip is in fluid communication with the sample pad. The sample strip is adapted to absorb a blood sample and deliver it to the sample pad via capillary action or the like. Thereafter, the blood can migrate to the conjugate pad, and mix with a reagent that can be released via a push button that is disposed on the top side of the housing.

The reagent includes a first antibody, which can bind with any hCG antigens present in the blood when the blood and the reagent are combined, creating a blood-reagent mixture. The mixture can then migrate toward the test pad, whereby the test pad includes a test portion and a control portion. The test portion includes a second antibody that is labeled, such as with dye. The dye is activated when the second antibody binds with the hCG antigens. When the concentration of the hCG antigens in the blood exceeds a predetermined threshold, a test window disposed on the top side is adapted to show a plus sign. Conversely, the test window is adapted to show a minus sign if the concentration of the hCG antigens falls below the predetermined threshold. Additionally, the control portion is adapted to display a symbol to visually indicate that the test was completed correctly, regardless of whether hCG is or is not present in the blood sample.

DESCRIPTION OF THE PRIOR ART

The prior art discloses a number of blood tests and various methods for measuring hCG hormone in female mammals to detect pregnancy. Some of these prior art references disclose direct agglutination reagents for pregnancy testing, wherein the agglutinates indicate a positive test for pregnancy when mixed with a urine or blood sample. Other prior art references disclose a method for detecting pregnancy that involves screening a biological sample of a woman for pregnancy markers. The prior art references, however, do not disclose a blood test kit that is suitable for home use. The foregoing is a list of prior art references deemed most relevant to the present disclosure, which are herein described for the purposes of highlighting and differentiating the unique aspects of the present invention, and further highlighting the drawbacks existing in the prior art.

Specifically, U.S. Pat. No. 4,003,988 to Hoff discloses a direct agglutination reagent for pregnancy testing. In one embodiment, the reagent comprises a liquid that can agglutinate when placed in contact with bodily fluids that contain hCG and polymeric latex carrier. The polymeric latex carrier is coated with rabbit anti-hCG serum and the reagent is buffered to a pH of 8.6 with a buffer that comprises piperazine dihydrochloride, water, and sodium hydroxide. Thus, Hoff does not disclose a blood test kit that is suitable for use at home to detect pregnancy. The present invention comprises a kit that comprises a housing having a test window for indicating the presence of hCG, a push button for releasing a reagent that react with hCG, and a sample pad for holding a blood sample.

U.S. Published Patent Application Number 2005/0148096 to Cole discloses methods of detecting pregnancy, wherein the methods include chemiluminescent assays for the pregnancy markers. The methods also comprise utilizing at least two capture antibodies that specifically bind different epitopes of the pregnancy marker in one assay. Chemiluminescence, however, must be performed in a lab, and therefore not suitable to be performed in a home setting. Thus, Cole fails to disclose an at-home pregnancy test kit.

U.S. Pat. No. 7,666,683 to Cole discloses a method of diagnosing a pregnancy, the method including the steps of measuring hyperglycosylated hCG in a pregnant woman and comparing the concentration of measured hyperglycosylated hCG with a predetermined value. If the measurement of hyperglycosylated hCG is above the predetermined value, the measurement indicates a normal pregnancy, while the measurement of hyperglycosylated hCG below the predetermined value indicates that the pregnancy is ectopic. The purpose and design of the present invention, however, differ from Cole in that the present invention discloses a device for detecting presence of hCG to determine whether the user is pregnant. Additionally, the method of Cole cannot be performed in a home setting.

U.S. Published Patent Application Number 2002/0013002 to D'Aurora discloses a pregnancy test based on saliva or other bodily fluids. The pregnancy kit includes a first vessel, a second vessel, and a third vessel, wherein the vessels are separated via removable surfaces. Thus, D'Aurora does not disclose a kit comprising a housing with a test window, a push button, and a sample pad, wherein the foregoing components are in fluid communication with each other.

Finally, U.S. Pat. No. 4,543,339 to O'Neill discloses a method of detecting pregnancy in a mammal at an early stage, which comprises the step of detecting physiological change consequent on increased activity of blood platelets resulting from the pregnancy. The enhanced activation of blood platelets is detected via: visualization with microscopy of the extent of morphological change; monitoring the release of excreted factors, such as calcium; spectrophotometric detection of the change in optical density of a solution containing platelets; or the determination of the onset of membrane adhesiveness by the ability of the platelets to cause agglutination of latex particles. Thus, O'Neill does not disclose a method of detecting pregnancy, wherein the method cannot be performed in a home setting.

The methods and devices disclosed in the prior art have several known drawbacks. These devices and methods are limited in that they must be used or performed in a lab setting. The present invention overcomes these limitations by disclosing an at-home blood test kit for detecting pregnancy. It is therefore submitted that the present invention is substantially divergent in design elements from the prior art, and consequently it is clear that there is a need in the art for an improvement to blood tests and various methods for measuring hCG hormone in female mammals. In this regard, the instant invention substantially fulfills these needs.

SUMMARY OF THE INVENTION

In view of the foregoing disadvantages inherent in the known types of blood tests and various methods for measuring hCG hormone in female mammals now present in the prior art, the present invention provides a new and improved at-home blood pregnancy test kit wherein the same can be utilized for detecting pregnancy in female mammals in a home setting.

It is therefore an object of the invention to provide a new and improved at-home blood pregnancy test kit that has all of the advantages of the prior art and none of the disadvantages.

Another object of the present invention is to provide a new and improved at-home blood pregnancy test kit that comprises a housing having a test window for viewing the pregnancy test results and a push button for releasing a reagent that reacts with hCG.

Yet another object of the present invention is to provide a new and improved at-home blood pregnancy test kit having a sample pad for holding a blood sample, a conjugate pad for holding a released reagent, and a test pad for detecting and indicating the presence of hCG, wherein the sample pad, the conjugate pad, and the test pad are in fluid communication.

Yet another object of the present invention is to provide a new and improved at-home blood pregnancy test kit that can perform hCG immunoassay using two types of antibodies and that is based on the sandwich principal.

Still yet another object of the present invention is to provide a new and improved at-home blood pregnancy test kit having a sample strip to deliver a blood sample to the sample pad.

Still yet another object of the present invention is to provide a new and improved at-home blood pregnancy test kit having a test window that displays a plus sign for showing a positive pregnancy result, a minus sign for showing a negative pregnancy result, and a control indicator for showing that the test was performed correctly.

Still yet another object of the present invention is to provide a new and improved at-home blood pregnancy test kit wherein the device may be readily fabricated from materials that permit relative economy and are commensurate with durability.

Other objects, features, and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein the numeral annotations are provided throughout.

Figure 2:
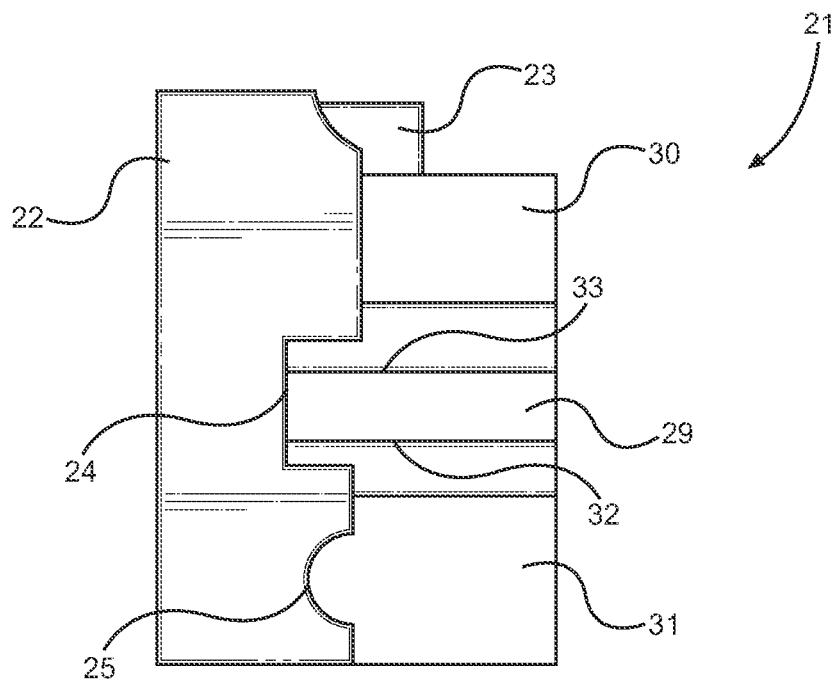

FIG. 1 shows a top down view of the present invention.
FIG. 2 shows a cutout view of the present invention.

DETAILED DESCRIPTION OF THE INVENTION

References are made herein to the attached drawings. Like reference numerals are used throughout the drawings to depict like or similar elements of the at-home blood pregnancy test kit. For the purposes of presenting a brief and clear description of the present invention, the preferred embodiment will be discussed as used to detect pregnancy in female mammals. The figures are intended for representative purposes only and should not be considered to be limiting in any respect.

Referring now to FIG. 1, there is shown a top down view of the present invention. The present invention comprises an at-home blood pregnancy test kit 21. The test kit 21 comprises a substantially rectangular housing 22 having an upper end 33 with a centrally located opening 34 along the length thereof, a lower end 35, a top side, a bottom side, and a hollow interior. In the illustrated embodiment, the opening 34 comprises a semi-circular cutout that extends towards the lower end 35. The opening 34 is adapted to provide access to the hollow interior of the housing 22. In a preferred embodiment, the housing 22 is composed of plastic or other suitable materials.

The opening 34 comprises a sample strip 23 held therebetween. The sample strip 23 comprises a piece of porous paper or sintered polymer that has the capacity to transport fluid spontaneously. The sample strip 23 comprises a first end and a second end. The first end of the sample strip 23 protrudes outward from the opening 34 so that the user can readily access the sample strip 23 and the sample strip 23 can collect a blood sample. It is contemplated that the user can prick her finger and dab the blood on the sample strip 23. The second end of the sample strip 23 extends inward into the housing 22 so that the sample strip 23 directly contacts a sample pad within the interior of the housing 22 to deliver the blood sample to the sample pad.

The housing 22 also comprises a test window 24. In the illustrated embodiment, the test window 24 comprises a rectangular cutout that allows the user to view a portion of the test pad, which is disposed within the interior of the housing 22. The test pad is adapted to display a plus sign 28 for showing a positive pregnancy result, a minus sign 27 for showing a negative pregnancy result, and a control indicator 26 for showing that the test was performed correctly.

The housing 22 further comprises a push button 25 that comprises a hollow interior for holding a reagent therein. It is contemplated that the reagent may be in a form of a solid capsule that can react with any hCG present in the blood sample. The push button 25 comprises a round protrusion that can be pressed towards the back side of the housing 22. When the push button 25 is pressed, the reagent can be crushed into a powder form and remain on the conjugate pad. Accordingly, the conjugate pad is directly subjacent to the push button 25. Alternatively, the reagent may be in a form of a liquid that can be released onto the conjugate pad when the push button 25 is pressed, whereby actuating the button 25 can break a seal within the interior of the push button 25 to allow the reagent to escape therefrom.

Referring now to FIG. 2, there is shown a cutout view of the blood pregnancy test kit 21 of the present invention. In one embodiment, the present invention comprises an hCG immunoassay to measure the presence of hCG in a blood sample. The hCG immunoassay of the present invention is based on the sandwich principal; comprising a first antibody binds and immobilizes hCG antigens in the blood sample, and a second antibody raised to a distant epitope and labeled with a dye. In other embodiments, however, the distant epitope may be labeled with an enzyme, or chemiluminescence agent, or other suitable substances that can mark the presence of hCG in a blood sample, such that the marking is visible to an unaided eye. The present invention is designed to primarily detect the regular placental form of the hCG because regular hCG is considered to be the key marker for pregnancy.

The sample strip 23 transports blood spontaneously into the sample pad 30. In some embodiments, the sample pad 30 may comprise a pad that acts as a sponge and holds an excess of blood sample. Once soaked, the blood migrates toward the test pad 29. The push button 25 is actuated to release the reagent at the conjugate pad 31, which then also travels towards the test pad 29. In this way, the reagent and the blood sample meet at the test pad 29. The reagent comprises a conjugate that is composed of particles that can chemically react with hCG, wherein the surface of the particles comprises a first antibody that can bind and immobilize hCG antigens.

Once the blood has migrated to the test pad 29, the blood can dissolve particles, so that the blood and the reagent can mix, creating a blood-reagent mixture. In this way, any hCG antigen present in the blood-reagent mixture can bind to the first antibody while migrating through the test pad 29. Accordingly, it is contemplated that the sample pad 30, the test pad 29, and the conjugate pad 31 are in fluid communication. Additionally, the sample pad 30 is directly adjacent to the test pad 29, which is also directly adjacent to the conjugate pad 31. In this way, the sample pad 30, the test pad 29, and the conjugate pad 31 directly contact one another. The sample pad 30, the test pad 29, and the conjugate pad 31 are coplanar and form a substantially contiguous surface when viewed from the side.

The test pad 29 is preferably composed of nitrocellulose, or a similar membrane. The test pad 29 comprises a test portion 33 and a control portion 32. Each of the test portion 33 and the control portion 32 comprises an indicator. Each indicator may include an antibody that has been immobilized. When the control portion 32 captures the blood-reagent mixture, the indicator of the control portion 32 can change color, thereby showing that reaction conditions and technology were operable, regardless of the presence of hCG. In the exemplary embodiment, the control portion 32 can show a marking such as a square shape when the indicator changes in color. The marking is visible through the test window 24. However, the control portion 32 may show other shapes or a line, depending upon embodiment.

The test portion 33 may comprise a second antibody that is labeled with a dye, which can be used to show a minus sign or a plus sign, depending upon whether hCG is present in the blood sample. When the second antibody binds with the hCG antigen, which is already bonded to a first antibody, the dye is actuated to mark the absence of the presence of hCG in the blood sample. If the hCG is absent or the concentration of hCG is under 5 mIU/ml, then the test will be considered negative, and a minus sign is shown. If the level of hCG is determined to be between 5 and 25 mIU/ml, then the test will be considered positive, and a plus sign is shown. The plus and minus signs are visible through the test window 24. In alternate embodiments, it is contemplated that the test portion 33 is adapted to change color when the level of hCG is determined to be between 5 and 35 mIU/ml.

Though the test window 24 and the test pad 29 is disposed between the sample pad 30 and the conjugate pad 31 in the illustrated embodiment, the test window 24 and the test pad 29 may be disposed at the lower end of the housing 22, depending upon embodiment. Furthermore, and in some embodiments, the present invention may further comprise a wick, which simply acts as a waste container for the blood sample.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above descriptions then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. A blood pregnancy test kit, comprising:
a housing comprising an interior volume, an upper end having a semi-circular cut-out extending radially inward, and a lower end, the lower end comprising a push button;
the semi-circular cut-out defining an opening providing access to the interior volume of the housing;

the push button comprising an interior volume and a seal, wherein the interior volume of the push button contains a reagent, the reagent comprising a first antibody that binds with human chorionic gonadotropin (hCG) antigen, wherein pressing the push button causes the seal to break, thereby releasing the reagent;

a sample strip positioned in the opening defined by the semi-circular cut-out, the sample strip comprising a first end extending outward from the opening and a second end extending into the interior volume of the housing;

a sample pad disposed in the interior volume, the sample pad in contact with the second end of the sample strip and in fluid communication with the sample strip;

wherein the sample strip is composed of a porous material configured to transport a blood sample to the sample pad;

wherein the sample pad is composed of a sponge-like material;

a test pad disposed in the interior volume of the housing, the test pad in contact with the sample pad and in fluid communication with the sample pad;

the test pad comprising a test portion having a second antibody that binds hCG antigen;

the housing further comprising a second cut-out portion positioned above the test pad, such that the test pad is viewable from an exterior of the housing;

a conjugate pad disposed in the interior volume of the housing, the conjugate pad in contact with the test pad and in fluid communication with the test pad;

wherein the conjugate pad is positioned directly subjacent the push button, such that the reagent is released onto the conjugate pad upon the push button being pressed;

wherein the test pad is positioned between the sample pad and the conjugate pad, wherein the sample pad, the test pad, and the conjugate pad are coplanar relative to each other and define a contiguous surface;

wherein the sample pad is configured to transport the blood sample to the test pad;

wherein the conjugate pad is configured to transport the reagent to the test pad;

wherein following transport of each of the reagent and the blood sample to the test pad, each of the reagent and the sample combine on the test pad to form a blood-reagent mixture and each of the first and second antibody bind with hCG antigen when hCG antigen is present in the sample.

2. The blood pregnancy test kit of claim 1, wherein the test pad comprises a control portion having an indicator to display a marking when the blood-reagent mixture contacts the control portion.

3. The blood pregnancy kit of claim 1, wherein the test pad exhibits a first symbol in order to indicate a positive pregnancy test when the presence of hCG antigen in the sample is above a predetermined threshold value; and
wherein the test pad exhibits a second symbol in order to indicate a negative pregnancy test when the presence of hCG antigen in the sample is below the predetermined threshold value.

4. The blood pregnancy test kit of claim 3, wherein the first symbol is a plus sign and the second symbol is a minus sign.

* * * * *